(12) United States Patent
Chono

(10) Patent No.: US 10,016,180 B2
(45) Date of Patent: Jul. 10, 2018

(54) ULTRASONIC IMAGE PROCESSING DEVICE

(71) Applicant: Hitachi, Ltd., Tokyo (JP)

(72) Inventor: Tomoaki Chono, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/503,173

(22) PCT Filed: Apr. 30, 2015

(86) PCT No.: PCT/JP2015/062965
§ 371 (c)(1),
(2) Date: Feb. 10, 2017

(87) PCT Pub. No.: WO2016/024422
PCT Pub. Date: Feb. 18, 2016

(65) Prior Publication Data
US 2017/0231601 A1 Aug. 17, 2017

(30) Foreign Application Priority Data

Aug. 15, 2014 (JP) ................................ 2014-165356

(51) Int. Cl.
*G06K 9/00* (2006.01)
*A61B 8/08* (2006.01)
(Continued)

(52) U.S. Cl.
CPC .............. *A61B 8/5207* (2013.01); *A61B 8/02* (2013.01); *A61B 8/486* (2013.01); *G06T 7/0012* (2013.01);
(Continued)

(58) Field of Classification Search
CPC .. A61B 8/08; A61B 8/02; A61B 8/486; A61B 8/5207; G06T 2207/10132; G06T 7/0012; G06T 7/60
(Continued)

(56) References Cited

U.S. PATENT DOCUMENTS 5,515,856 A 5/1996 Olstad et al.
9,514,531 B2 * 12/2016 Chono ................... A61B 6/469
(Continued)

FOREIGN PATENT DOCUMENTS

| JP | 2001120552 A | 5/2001 |
| JP | 2006223558 A | 8/2006 |
| JP | 4656392 B2 | 3/2011 |

OTHER PUBLICATIONS

International Search Report dated Sep. 1, 2015 for International Patent Application No. PCT/JP2015/062965.
(Continued)

*Primary Examiner* — Tom Y Lu

(57) ABSTRACT

An extraction period specification unit specifies an extraction period (extraction section) for an M-mode image. A model expansion/contraction unit establishes a contour model (initial configuration) in relation to the specified extraction period while expanding/contracting the contour model in the direction of the time axis so as to conform with the extraction period. A node position change unit performs, for each node forming a plurality of node strings included in the established contour model, an edge (contour) search while successively changing the positions of the nodes, resulting in the formation of a revised contour model comprising a plurality of nodes at an edge detection position. A trace unit carries out interpolation on a plurality of node strings included in the revised contour model, thereby generating a plurality of trace lines simulating a plurality of contour lines.

9 Claims, 10 Drawing Sheets

(51) Int. Cl.
   *A61B 8/02*   (2006.01)
   *G06T 7/00*   (2017.01)
   *G06T 7/60*   (2017.01)
(52) U.S. Cl.
   CPC ...... *G06T 7/60* (2013.01); *G06T 2207/10132* (2013.01)
(58) Field of Classification Search
   USPC .......................................................... 382/128
   See application file for complete search history.
(56) References Cited

U.S. PATENT DOCUMENTS

| | | | |
|---|---|---|---|
| 9,826,959 B2* | 11/2017 | Miyachi | A61B 8/0858 |
| 2005/0288589 A1* | 12/2005 | Houle | A61B 8/00 600/450 |
| 2007/0135705 A1* | 6/2007 | Lorenz | A61B 5/055 600/410 |
| 2011/0044522 A1* | 2/2011 | Fancourt | G06T 7/2033 382/131 |
| 2012/0041313 A1* | 2/2012 | Tanaka | A61B 8/04 600/443 |
| 2015/0320399 A1* | 11/2015 | Chono | A61B 8/5223 382/131 |

OTHER PUBLICATIONS

Extended European Search Report for International Application No. PCT/JP2015/062965, dated Mar. 23, 2018, 9 pages.

Malpica N. et al. "A snake model for anatomic M-mode tracking in echocardiography". Image and Signal Processing Analysis, 2003. Sep. 18, 2003, 5 pages.

* cited by examiner

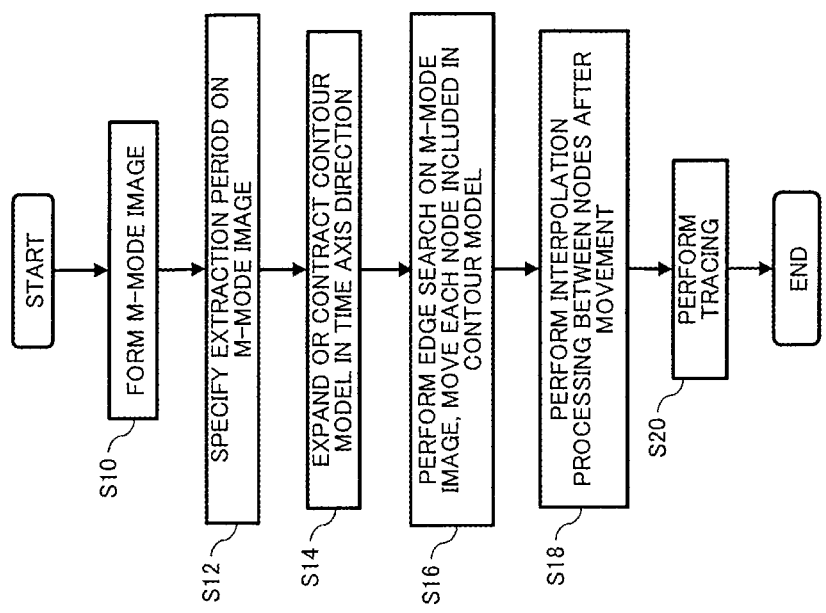

ULTRASONIC IMAGE PROCESSING DEVICE

CROSS-REFERENCE TO RELATED APPLICATIONS

This application is a national phase claiming the benefit of and priority to International Patent Application No. PCT/JP2015/062965, entitled "ULTRASONIC IMAGE PROCESSING DEVICE", filed Apr. 30, 2015, which claims priority to Japanese Patent Application No. 2014-165356, entitled "ULTRASONIC IMAGE PROCESSING DEVICE", filed Aug. 15, 2014, which are hereby incorporated by reference in their entireties.

TECHNICAL FIELD

The present invention relates to an ultrasonic image processing device, and particularly to an ultrasonic image processing device that processes an M-mode image representing tissue motion in a subject.

BACKGROUND

An ultrasonic diagnostic device is a device that transmits and receives ultrasound to and from the subject, and forms an ultrasonic image based on received signals obtained in this way. Ultrasonic images formed by the ultrasonic diagnostic device include various types of images, and an M-mode image is one of them. An M-mode image is an image representing tissue motion in the subject. In an M-mode image, for example, the vertical axis is the depth axis, and the lateral axis is the time axis, and a high brightness (or low brightness) line (contour line) extending in the time axis direction shows the state of motion of a tissue toward the depth direction. In addition, an M-mode image representing tissue motion on an observation line optionally set on a B-mode tomography image is also known.

The M-mode image is used to measure the LA/AO ratio, for example. The LA/AO ratio is an index for assessing the shape of the heart, and it is a ratio between the left atrial dimension (LA) at the end of cardiac systole and the aortic dimension (AO) at the end of cardiac diastole. In conventional measurement of the LA/AO ratio, an examiner specifies positions of both left atrial walls at the end of cardiac systole and positions of both aortic walls at the end of cardiac diastole by, for example, manually moving a cursor on an M-mode image including contour lines representing movement of positions of the aortic walls and the left atrial walls.

Because, conventionally, the examiner has to manually specify measurement points in the M-mode image, there arises a problem in that measurement is time-consuming, for example. Therefore, in order to automatically set the measure points, there has been proposed a technique of performing automatic tracing of a contour line included in an M-mode image.

For example, Patent Document 1 discloses determining one point at a position on a tissue border on an M-mode image, comparing a luminance value of that point with luminance values of five neighboring pixels located at positions shifted from that point by one pixel in the time axis direction (next time point), and setting, from among the five neighboring pixels, a pixel having the smallest difference in luminance value as a tissue border in a next iteration. By repeating this processing, a line indicating motion of the tissue border is traced. On the M-mode image, the contour line is typically a relatively smooth curve that periodically flows in the time axis direction. The technique disclosed in Patent Document 1 uses such a characteristic, and sequentially searches positions of the tissue border in the time axis direction.

CITATION LIST

Patent Literature

Patent Document 1: JP 4656392 B

SUMMARY

Technical Problem

If extraction of a contour line is performed on an M-mode image in an ultrasonic diagnostic device or an information processing device that processes an ultrasonic image, improvement of extraction accuracy or reduction in extraction time is required. Meanwhile, because the sweep rate of an M-mode image varies, and the heartbeat rate is not constant, it is desired to achieve a contour line extraction method that is independent from them. In addition, it is recognized that the technique disclosed in Patent Document 1 has a problem that if extraction of a contour line is performed over a long distance, the extraction becomes susceptible to noise or the like.

An object of the present invention is to extract a contour line on an M-mode image with high accuracy. Alternatively, an object of the present invention is to reduce processing time of extracting a contour line on an M-mode image. Alternatively, an object of the present invention is to simultaneously extract, per heartbeat, a plurality of contour lines that periodically move on an M-mode image in sync with heartbeats.

Solution to Problem

An ultrasonic image processing device according to the present invention has a specifying unit that specifies, in an M-mode image including a contour line as a motion curve, an image portion that includes an extraction portion of the contour line, and an extracting unit that applies a contour model including a node string to the image portion including the extraction portion, thereby extracting the extraction portion of the contour line, and the ultrasonic image processing device is characterized in that the extracting unit includes an initial setting unit that configures initial settings of the contour model for to the image portion, and a model deforming unit that performs contour search on the M-mode image for each of nodes included in the node string after the initial settings, thereby fitting the node string to the extracting portion and forming a modified contour model.

With the above-described structure, by applying the contour model including the node string to a partial image in the M-mode image, the extraction portion included in the partial image is extracted. More specifically, the contour model is a model for contour search including at least one node string (preferably, a plurality of node strings), and each node string is composed of a plurality of nodes arranged in the time axis direction. Each node functions as a contour search point, and initial set positions of the nodes with respect to the partial image define search start positions. The presence of a contour is searched by the node by sequentially changing positions of the node on the partial image. Various known methods can be used as a contour detection method. In any case, a plurality of positions (contour points) on the extraction portion are extracted individually by the plurality of nodes. After such processing, a modified contour model including the node strings fitted to the extraction portion can be obtained.

If, in the above-described structure, contour search is performed by the plurality of nodes in parallel, search time can be reduced as compared with the case where search is performed successively from one end to the other end of the contour line. In that case, if each node performs contour search independently; that is, if each node performs search without being affected by the search results of other nodes, it is possible to avoid a problem of a chain of errors in contour detection due to noise or the like. However, upon determination of a search range and the like, positions of other nodes and others may also be referenced. By adopting the contour model, it is possible to determine an initial form of a node string or an initial arrangement of a plurality of node strings in accordance with a standard form or a standard structure of the extraction portion to be extracted. In doing so, it is possible to obtain the advantage that contour search can be efficiently carried out by the individual nodes. Moreover, because it becomes possible to narrow the search range effectively, noise-resistant, highly reliable processing can be achieved.

Preferably, the initial setting unit includes a size adjusting unit that adjusts the size of the contour model in the time axis direction according to the length of the extraction portion in the time axis direction, and a model positioning unit that positions the contour model obtained after size adjustment on the image portion.

The length of the extraction portion in the time axis direction changes according to the sweep rate and the heartbeat rate. Therefore, in the above-described structure, during the initial setting of the contour model, the size adjusting unit adjusts the size of the contour model in the time axis direction according to the length of the extraction portion in the time axis direction. After that, the model positioning unit positions the size-adjusted contour model on the partial image. The size adjustment eliminates the necessity of generating and storing in advance a plurality of contour models having different time lengths. The size adjustment can be achieved, for example, by expanding and contracting an original model and computing a size-adjusted model. It is preferable that the positions of the nodes in the time axis direction are defined, for example, as relative positions with respect to the entire period of the contour model so that the relative positional relationship between the nodes in the time axis direction is maintained even if the contour model is expanded or contracted in the time axis direction. Moreover, preferably, the size of the contour model in the distance axis direction can also be adjusted to the scale of the distance axis.

Preferably, the model deforming unit performs the contour search in the distance direction that is vertical to the time axis direction, for each node included in the positioned node string. Although contour search may be performed widely in two dimensions for each node, if contour search is limited to mainly the distance direction, or restricted to the distance direction only, the search efficiency can be improved. Even in that case, because the size adjustment of the contour model is already performed; that is, the arrangement of the plurality of nodes are adjusted to the time length of the extraction portion, it is possible to search the entire extraction portion accurately by the plurality of nodes. For example, if the plurality of nodes are arranged at equal intervals in the time axis direction, the equal intervals are maintained, thereby maintaining equal search resolution in the time axis direction.

Preferably, the model deforming unit performs, for each node included in the positioned node string, the contour search in a neighboring range of an initial set position of a node. With this structure, the search range is limited, for each node, to be within the neighboring range in the distance direction. In doing so, the problem of unnecessary increase of the search range can be avoided, and the search time can be reduced. The neighboring range is basically a range expanded to both sides of the initial set position along the distance direction, and the size of the neighboring range may be set for each node separately, or a uniform neighboring range may be set for the plurality of nodes.

Preferably, the initial setting unit further includes a model generating unit that generates an original contour model based on a plurality of modified contour models formed in the past, and the size adjusting unit adjusts the size of the original contour model in the time axis direction. With this configuration, it is possible to generate, through the plurality of modified contour models, an original contour model that reflects a plurality of extraction portions (actual contour form) that were objects for fitting in the past. Therefore, when the contour model obtained after the size adjustment based on the original contour model is applied to the partial image, this increases the likelihood that initial set positions of the plurality of nodes are brought closer to an actual extraction portion.

Preferably, the model deforming unit determines the size of the neighboring range in which the contour search is performed, based on a plurality of modified contour models formed in the past. For example, if positions of a certain node are concentrated to a narrow range in a plurality of modified contour models formed in the past, it can be said that a contour position corresponding to that node is highly likely to be within a corresponding range in an M-mode image which is an object for extraction this time. Therefore, by determining a contour search range based on the past modified contour models, it becomes possible to further narrow the contour search range. In doing so, the search efficiency is further improved.

Preferably, the M-mode image includes a plurality of contour lines, the contour model includes a plurality of node strings for extracting a plurality of extraction portions of the plurality of contour lines, and the model deforming unit performs contour search for each node included in the plurality of node strings, and fits the plurality of node strings to the plurality of extraction portions, respectively.

With the above-described structure, by using the contour model having the plurality of node strings, it becomes possible to extract the plurality of extraction portions included in the image portion simultaneously or collectively. The plurality of extraction portions, taken as a whole, have a two-dimensional pattern expanding in the time axis and the space axis, and a contour pattern composed of the plurality of node strings (two-dimensional node arrays) can be located thereon. Therefore, it becomes easier to locate the contour model on the extraction portions even if a part of the plurality of extraction portions are unclear, or even if the plurality of extraction portions are close or come into mutual contact.

Preferably, the ultrasonic image processing device according to the present invention has a tracing unit that generates a trace line which simulates the extraction portion, by interpolation processing based on the node string fitted to the extraction portion.

Preferably, the specifying unit specifies the image portion based on heartbeat information of the subject. In doing so, one or more heartbeats of interest are specified by heartbeat information. The specifying unit may also specify the image portion or a section to be processed based on an input by the user who has observed an electrocardiogram displayed parallel to the M-mode image.

Advantageous Effect of Invention

With the present invention, it is possible to perform extraction of a contour line on an M-mode image with high accuracy. Alternatively, it is possible to reduce processing time of extracting a contour line on an M-mode image. Alternatively, it is possible to simultaneously extract, per heartbeat, a plurality of contour lines that move periodically on an M-mode image in sync with heartbeats.

BRIEF DESCRIPTION OF DRAWINGS

FIG. 10 is a flowchart showing an operational flow of the ultrasonic diagnostic device according to the present embodiment.

DESCRIPTION OF EMBODIMENTS

An embodiment of the present invention will be explained below.

Figure 1:
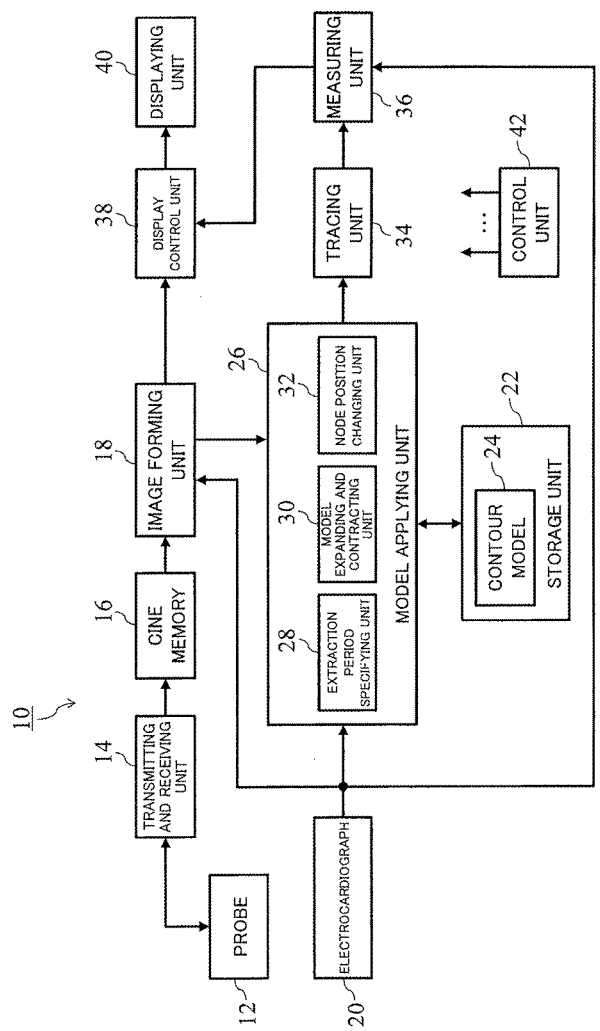
FIG. 1 is a schematic block diagram showing an ultrasonic diagnostic device according to the present embodiment.

FIG. 1 is a schematic block diagram of an ultrasonic diagnostic device 10 serving as an ultrasonic image processing device according to the present embodiment. The ultrasonic diagnostic device 10 is a medical device which is generally located in medical organizations, such as hospitals, and is used to conduct ultrasonic diagnosis of a subject. The ultrasonic diagnostic device 10 has a function of forming an M-mode image representing motion of a tissue border in the subject. In the present embodiment, the ultrasonic diagnostic device 10 forms an M-mode image, and performs measurement of the above-noted LA/AO ratio using the M-mode image.

A probe 12 is an ultrasonic probe that transmits and receives ultrasound to and from the subject. The probe 12 has a transducer array composed of a plurality of transducers. Each transducer included in the transducer array is vibrated by a corresponding one of a plurality of transmitted signals from a transmitting and receiving unit 14, and generates an ultrasound beam. In addition, the transducer array receives reflected echo from an ultrasound transmitting and receiving region, converts acoustic signals to received signals which are electric signals, and outputs the received signals to the transmitting and receiving unit 14. In the present embodiment, the probe 10 transmits and receives ultrasound to and from the heart of the subject.

The transmitting and receiving unit 14 transmits to the probe 12 a plurality of transmitted signals which excite the plurality of transducers of the probe 12, to thereby generate ultrasound in the probe 12. The transmitting and receiving unit 14 also performs phasing and adding processing on the plurality of received signals obtained from the plurality of transducers which received reflected echo, and forms beam data arranged in a scanning direction of the ultrasound beam. The beam data are composed of a plurality of reflected echo signals arranged in the depth direction. As such, the transmitting and receiving unit 14 has functions as a transmit beamformer and a receive beamformer.

In the present embodiment, an image forming unit 18 described below forms an M-mode image. A B-mode image is formed before an M-mode image is formed, and, on the B-mode image, an observation path that is an object for an M-mode image is set. After the observation path is set, ultrasound is transmitted and received to and from the observation path.

A cine memory 16 stores a plurality of beam data items from the transmitting and receiving unit 14. The cine memory 16 has a structure like, for example, that of a ring buffer, and sequentially stores the beam data items which are input in chronological order. The cine memory 16 stores the beam data items from the most recent one to older ones obtained over a certain period of time in the past.

The image forming unit 18 is, for example, a digital scan converter (DSC) or the like, and forms an ultrasonic image as a biological image based on the beam data items stored in the cine memory 16. Ultrasonic images formed in the image forming unit 18 include, for example, a B-mode image which is a tomographic image of a tissue in the subject, in addition to an M-mode image.

An M-mode image is formed by converting the beam data items based on the received signals from the observation path to luminance values according to the intensity of reflected echo, and arranging them in chronological order. Because the intensity of reflected echo becomes larger on the tissue borders, such as, for example, the vascular wall and the cardiac wall, their positions are displayed in high brightness. Subsequently, beam data strings sequentially obtained on the observation path are subjected to the same processing and swept on a displaying unit 40, and a high luminance line extending in the time axis direction is formed on the M-mode image. The high luminance line becomes a contour line indicating tissue motion in the subject.

M-mode images are formed so as to differ in scale in the time axis direction according to the sweep rate set by the user. If the sweep rate is large, a period of time for display on one M-mode image becomes relatively short, whereas if the sweep rate is small, a period of time for display on one M-mode image becomes relatively long. Therefore, contour lines included in the M-mode images also differ in expansion and contraction rate in the time axis direction according to the sweep rate.

In the present embodiment, the image forming unit 18 forms an M-mode image based on beam data passing through the aortic valve and the left atrium of the heart of the subject. Therefore, in the M-mode image formed in the present embodiment, chronological changes in positions of the aortic wall, the aortic valve, and the left atrial wall are represented by contour lines extending in the time axis direction. The contour lines differ from, for example, real two-dimensional contours of the tissues, and are artificial contours formed by sweeping. The contour lines have periodic forms in accordance with the sweep rate and the heartbeat rate. That is, each contour line is formed of connected similar waveform patterns over a plurality of heartbeats.

An electrocardiograph 20 outputs electrocardiographic data indicating a state of pulses of the heart of the subject. The electrocardiograph 20 has an electrode and measures the electromotive force of the heart of the subject when the electrode is attached to the subject. Data indicating the measured electromotive force are output as electrocardiographic data.

A storage unit 22 is composed of, for example, a hard disk, a ROM, or a RAM, and stores programs executed in the ultrasound device 10 or data to be processed in the ultrasonic diagnostic device 10. The storage unit 22 also stores a contour model 24.

The contour model 24 is a model for extracting a contour structure on the M-mode image. The contour model 24 corresponds to a relevant contour structure within a predetermined period of time (i.e., a part of the contour structure), and, in the present embodiment, it corresponds to a contour structure for one heartbeat period. Specifically, an M-mode image has a form like an aggregate of a large number of contour lines arranged in the depth direction, and, in the present embodiment, a particular plurality of contour lines among them (target contour lines) are to be subjected to extraction processing. More specifically, among the plurality of target contour lines, a plurality of line segments within a particular cardiac cycle specified by the user (target line segments) are to be subjected to extraction processing. Meanwhile, the contour model is composed of a plurality of node strings corresponding to the plurality of target line segments, and an arrangement of the plurality of node strings is defined as a standard arrangement for the plurality of target line segments. In fact, a contour model is provided for each type of measurement to achieve a measurement of concern. The contour model 24 is provided in advance and stored in the storage unit 22.

In the present embodiment, as described above, concerning the M-mode image, the plurality of contour lines indicating motion of the aortic wall, the aortic valve, and the left atrium are set as the target lines, and there is provided the contour model 24 including the plurality of node strings corresponding to the plurality of target line segments that are parts of each target line. Each node string includes a plurality of nodes. In the contour model 24, as described later, the plurality of node strings are arranged in the depth direction (distance direction). Therefore, the contour model 24 has a plurality of nodes arranged in two dimensions, along the time axis direction and the depth direction.

Moreover, although, in the present embodiment, the contour model 24 includes a plurality of node strings, it is also possible to adopt a form in which the contour model 24 includes only one node string. Furthermore, a plurality of contour models 24 are preferably provided according to measurements types or characteristics of the subject (such as age and sex). The contour model 24 will be explained in detail later with reference to FIG. 4.

A model applying unit 26 applies the contour model 24 to the M-mode image formed by the image forming unit 18, and fits the contour model 24 to the plurality of target line segments included in the M-mode image, to thereby deform the contour model 24. The plurality of target line segments are extracted from the M-mode image in this manner. The M-mode image treated by the model applying unit 26 is an M-mode image which is frozen at a predetermined time point by the user and in which the sweep is stopped.

An extraction period specifying unit 28 included in the model applying unit 26 specifies, in the M-mode image, an extraction period which is a period for extracting the target line segments. In the present embodiment, the extraction period is specified as an image portion having a certain area including the plurality of target lines on the M-mode image. In the present embodiment, a period between peaks of R wave of an electrocardiographic waveform; that is, one heartbeat period, is defined as an extraction period, based on signals from the electrocardiograph 20. The extraction period may also be a period of time other than one heartbeat period, and may be a two heartbeat period, for example. It is preferably set to be a period of time that fits the time length of a prepared model.

A model expanding and contracting unit 30 included in the model applying unit 26 expands and contracts the contour model 24 in the time axis direction according to the specified extraction period. Because, as described above, M-mode images have different scales in the time axis direction according to the sweep rate, the lengths in the time axis direction differ according to the sweep rate even in the same one heartbeat period, for example. The model expanding and contracting unit 30 expands or contracts the contour model 24 in the time axis direction, thereby enabling the contour model 24 to be applied to the M-mode image appropriately, regardless of the setting of the sweep rate. In doing so, there is no need to provide a plurality of models having different time lengths.

A node position changing unit 32 included in the model applying unit 26 performs edge search for each node included in the contour model 24, which was applied to the M-mode image and subjected to expansion and contraction processing (i.e., subjected to initial setting), and moves positions of the nodes onto the plurality of target line segments included in the M-mode image formed by the forming unit 18. More specifically, the positions of the nodes included in the node strings are changed so that the plurality of node strings included in the contour model 24 fit the plurality of target line segments in the M-mode image.

Detailed processing contents in the model applying unit 26 will be explained in detail later with reference to FIGS. 5 to 8.

A tracing unit 34 traces the target line segments in the M-mode image, based on the plurality of node strings which were applied and fitted to the M-mode image by the model applying unit 26 and constitute a modified contour model. Specifically, tracing is performed by carrying out interpolation point adding processing between adjacent nodes included in the individual node strings of the modified contour model. The tracing unit 34 performs tracing processing to thereby form a plurality of trace lines that are approximate to the target line segments included in the M-mode image.

A measuring unit 36 performs measurement based on the trace lines formed by the tracing unit 34. In the present embodiment, the LA/AO ratio is measured. For example, the measuring unit 36 specifies, on the plurality of trace lines, positions of the heart of the subject at the end of cardiac systole and at the end of cardiac diastole, based on an electrocardiographic waveform. Subsequently, the measuring unit 36 measures the aortic dimension at end-systole and the left atrial dimension at end-diastole based on the plurality of trace lines. The processing in the tracing unit 34 and the measuring unit 36 will be explained in detail later with reference to FIG. 9.

A display control unit 38 performs displaying processing on various images including the M-mode image formed by the image forming unit 18 and, for example, on numerical values indicating the measurement results by the measuring unit 36, and causes the displaying unit 40 to display them. A control unit 42 is, for example, a CPU, and controls the entire ultrasonic diagnostic device 10.

Although, in the present embodiment, the ultrasonic diagnostic device 10 is used as an ultrasonic image processing device, the ultrasonic diagnostic device may forward a received signal to a personal computer (PC), and the PC may form data of an M image, apply a contour model to the M-mode image, deform the contour model, and perform measuring processing. In this case, the PC is equivalent to the ultrasonic image processing device.

Moreover, among the components shown in FIG. 1 (units with reference signs), the image forming unit 18, the model applying unit 26, the tracing unit 34, and the measuring unit 36 can all be achieved using hardware, such as electric-electronic circuits and processors, and in such achievement, devices, such as memories, may also be used, if necessary. Further, functions corresponding to the above-described units may also be achieved by cooperation between hardware, such as a CPU, processor, and memory, and software (program) that defines operation of the CPU and the processor. A preferable specific example of the displaying unit 40 is a liquid crystal display, for example. The control unit 42 can be achieved by cooperation between hardware, such as, for example, a CPU, processor, and memory, and software (program) that defines operation of the CPU and the processor.

Figure 2:
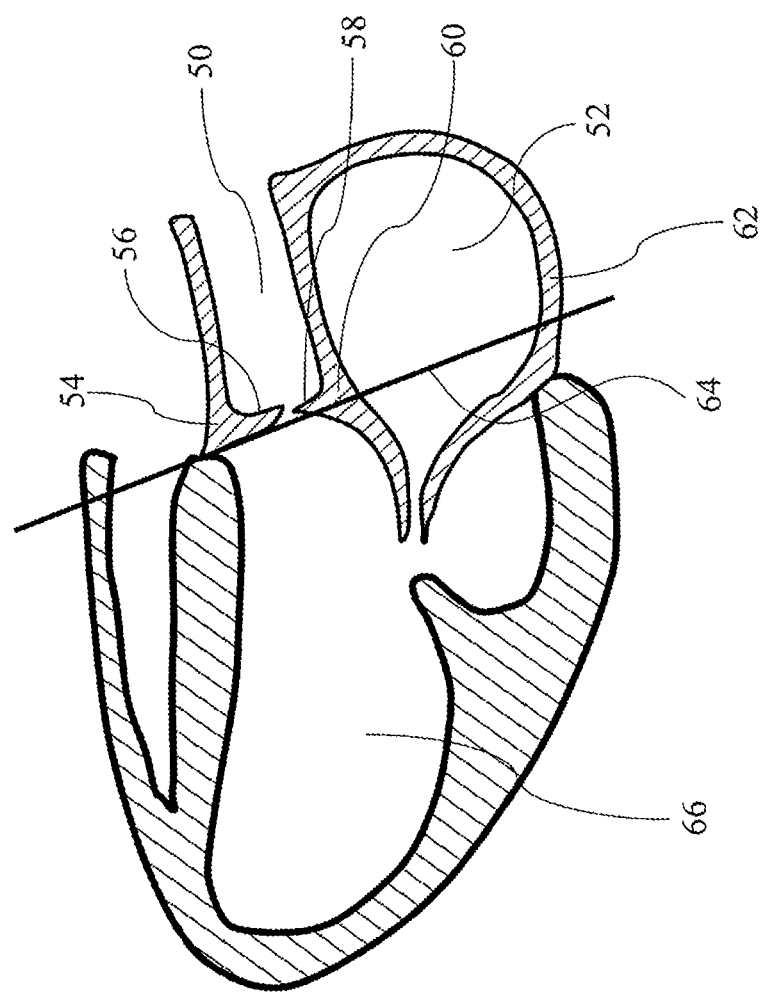
FIG. 2 is a diagram showing an observation path in the present embodiment.

FIG. 2 is a diagram showing an observation path 64 in the present embodiment. FIG. 2 is a sectional view of the heart, and shows an aorta 50, a left atrium 52, and a left ventricle 66. Since, in the present embodiment, the diameter of the aorta 50 and the diameter of the left atrium 52 are measured, the observation path 64 is set so as to pass through an anterior aortic wall 54, an anterior aortic valve 56, a posterior aortic valve 58, a posterior aortic wall (which also serves as an anterior left atrial wall) 60, and a posterior left atrial wall 62. An M-mode image is formed based on beam data along the observation path 64.

Figure 3:
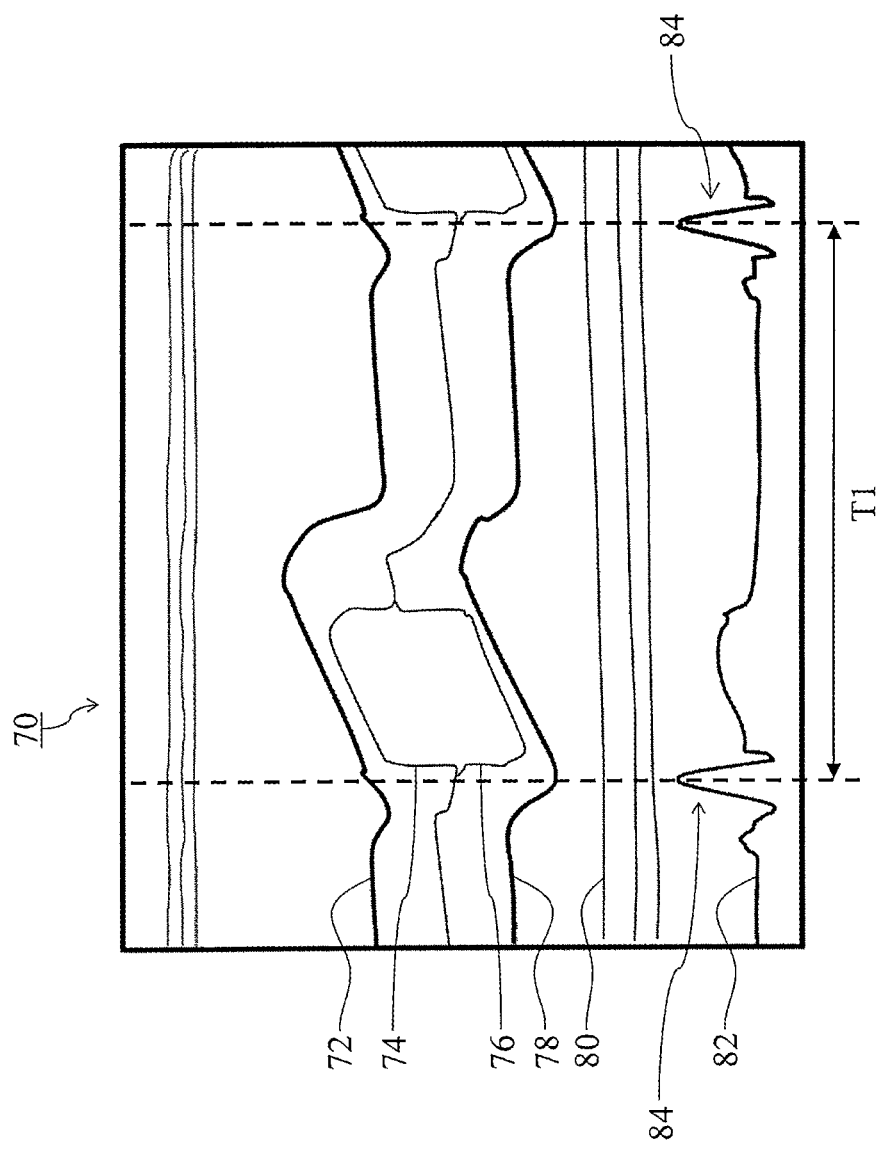
FIG. 3 is a diagram showing an example of an M-mode image in the present embodiment.

FIG. 3 is a diagram showing an M-mode image 70 formed in the present embodiment. FIG. 3 will be explained with reference to FIG. 1 and FIG. 2. In the M-mode image 70, the lateral axis is the time axis, and the vertical axis is the depth axis. Contour lines 72, 74, 76, 78, and 80 displayed in high brightness represent the motion of tissues in the subject. Specifically, the contour line 72 represents the motion of the anterior aortic wall 54; the contour line 74 represents the motion of the anterior aortic valve 56; the contour line 76 represents the motion of the posterior aortic valve 58; the contour line 78 represents the motion of posterior aortic wall 60; and the contour line 80 represents the motion of the posterior left atrial wall 62. Moreover, the aortic valve opens and closes repeatedly according to the heart rate. Because the aortic valve opens at early systole, the contour lines 74 and 76 are branched into two at early systole. However, in other time phases, the aortic valve closes, and therefore, the contour lines 74 and 76 are almost integrated.

In addition, the M-mode image 70 includes an electrocardiographic waveform 82 formed based on electrocardiographic data obtained by the electrocardiograph 20. Since, in the present embodiment, the contour line for one heartbeat period is extracted, the extraction period specifying unit 28 detects peaks of R wave 84 from the electrocardiographic waveform 82, and specifies a period between the peaks of the R wave 84 as an extraction period T1.

Figure 4:
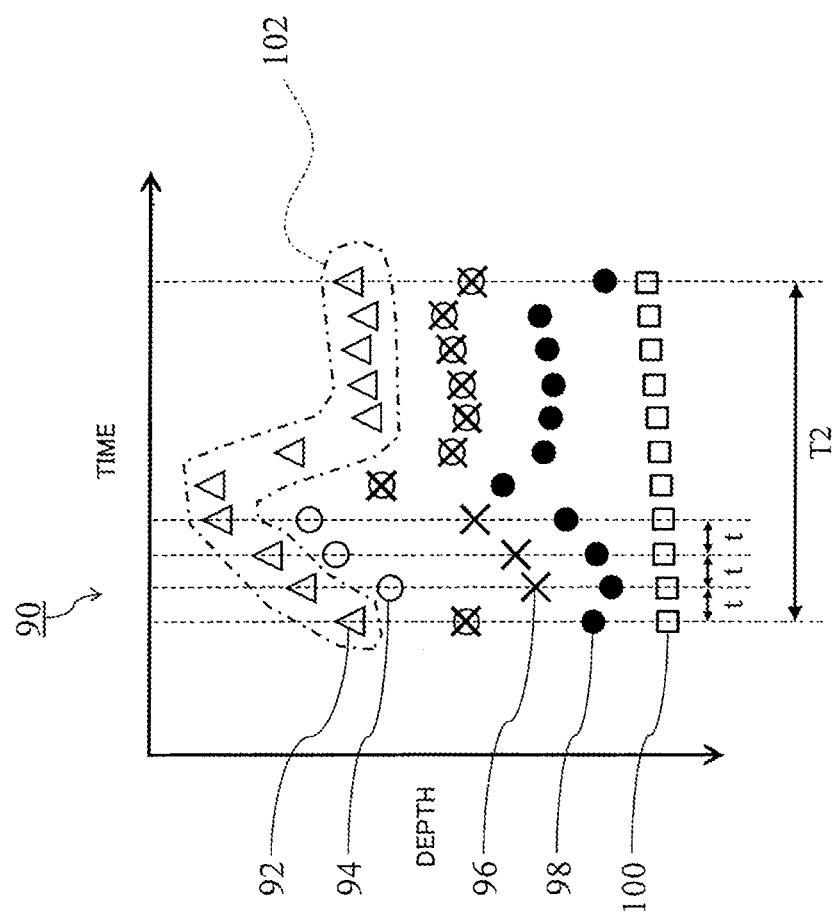
FIG. 4 is a conceptual diagram showing a contour model.

FIG. 4 is a conceptual diagram showing an example of a contour model. FIG. 4 is a diagram showing an original contour model before, for example, the model expanding and contracting unit 30 performs processing. In FIG. 4, the lateral axis is the time axis, and the vertical axis is the depth axis. A contour model 90 includes a plurality of node strings for extracting contour lines of the aortic wall, the aortic valve, and the left atrial wall for one heartbeat period T2. For example, a node string 102 including a plurality of nodes 92 indicated by triangles corresponds to a contour line of the anterior aortic wall 54, and the plurality of nodes 92 are search points for extracting that contour line. The plurality of nodes 92 included in the node string 102 are plotted along an average shape of the contour line of the anterior aortic wall 54. Similarly, a plurality of nodes 94 indicated by white circles correspond to the anterior aortic valve 56; a plurality of nodes 96 indicated by X-marks correspond to the posterior aortic valve 58; a plurality of nodes 98 indicated by black circles correspond to the posterior aortic wall 60; and a plurality of nodes 100 indicated by rectangles correspond to the posterior left atrial wall 62. As shown in FIG. 4, the plurality of nodes included in the contour model 90, taken as a whole, form a two-dimensional arrangement in the time axis direction and the depth direction.

Any number of nodes may be included in each node string included in the contour model 90. Although the larger number of nodes can represent the shape of the contour line in more detail, in that case, it takes more time to perform extraction processing of the contour line. On the other hand, if the number of nodes is smaller, the shape of the contour line extracted by the model becomes rougher, but processing time can be reduced.

Each node included in the contour model 90 has time information indicating a relative time point with respect to the one heartbeat period T2, and depth information indicating the depth of the tissue at that time point. In the contour model 90 in the present embodiment, intervals t between the nodes included in each node string are uniform in the time axis direction; that is, they are equal intervals. The interval t is a unit obtained when the one heartbeat period T2 is divided equally (in the contour model 90, the period is divided into ten equal parts). In the contour model 90, the plurality of nodes are plotted at intervals t, which are obtained by dividing the one heartbeat period T2 into ten equal parts, and order information indicating the order of nodes in the node string 102 in the time axis direction is set, to thereby provide each node with time information indicating a relative time point with respect to the one heartbeat period T2.

Although the contour model 90 may be made, for example, by the user, it is preferably formed based on edge positions detected in the past. For example, pieces of depth information of the nodes included in the modified contour model obtained by fitting processing by the model applying unit 26 may be stored in the storage unit 22, to thereby determine the depths of the nodes of the contour model 90 (initial positions in the depth direction) based on the plurality of accumulated pieces of depth information. For example, the pieces of depth information may be stored separately for each node included in the modified contour model, to thereby calculate an average value of the depth for each node, and set the average value as an initial depth position for a relevant node in the contour model 90. By determining the position of the node based on the edge positions detected in the past, it is possible to set an initial position of each node included in the node string of the contour line 90 at a position closer to a contour line to be extracted, and reduce the search distance in edge search in which the node is set as a start point. In doing so, the efficiency in edge search is improved.

Figure 5:
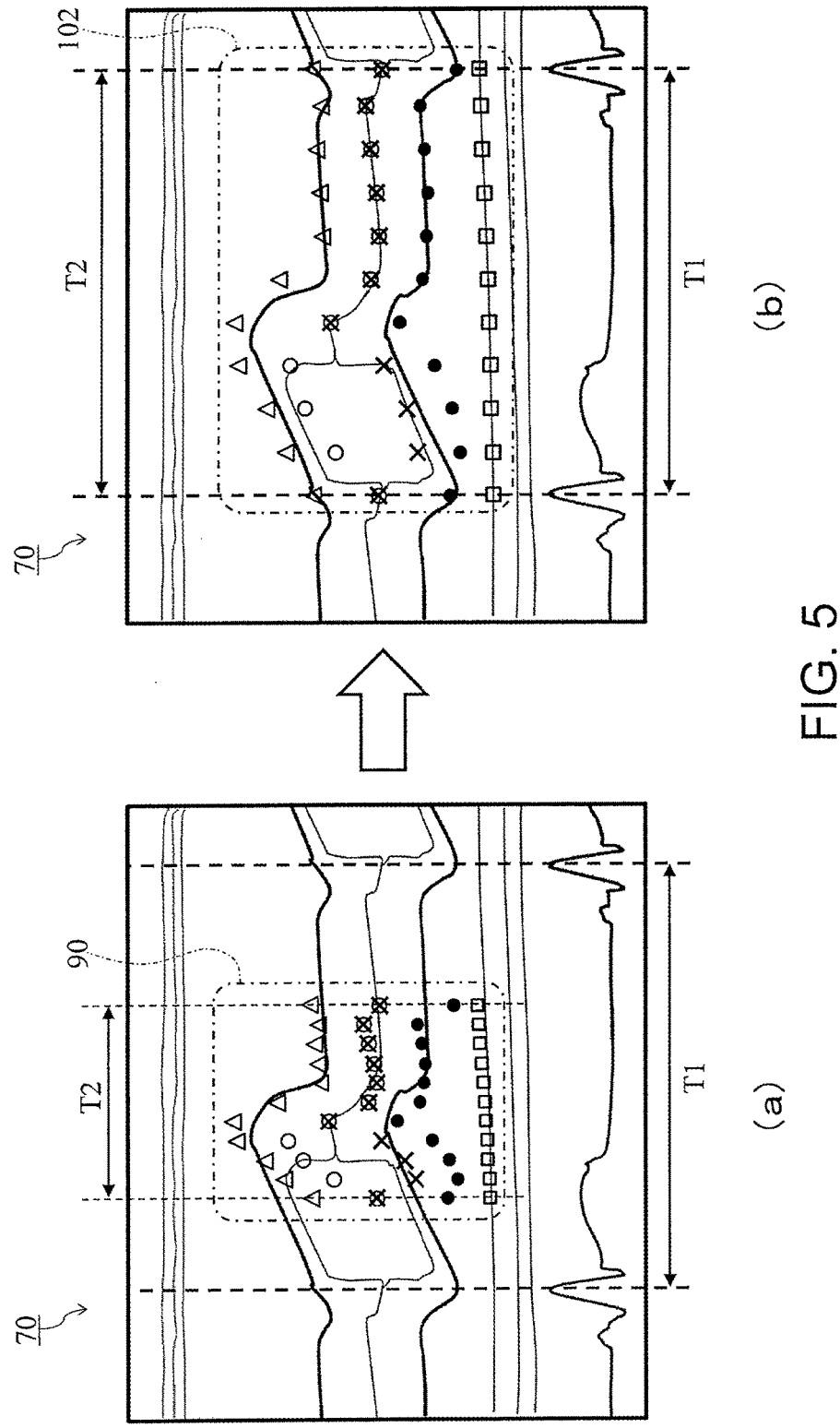
FIG. 5 is a conceptual diagram showing a state in which the contour model is expanded along the time axis direction.

Hereinafter, processing performed in the model applying unit 26 will be explained based on FIGS. 5 to 9 and with reference to FIG. 1. FIG. 5 is a conceptual diagram showing a state in which the contour model 90 is expanded in the time axis direction. In addition, the present embodiment will be explained based on an example where the contour model 90 is superimposed on the M-mode image 70.

First, the model applying unit 26 configures initial settings of a contour model. The initial settings include application of the contour model to an M-mode image, and expansion and contraction processing by the model expanding and contracting unit 30. If the contour model is formed based on the past measurement results or the like, the initial settings may also include formation of that contour model. As shown in FIG. 5(*a*), the model applying unit 26 superimposes the contour model 90 on the M-mode image 70. As described above, because the M-mode image 70 is changed in scale in the time axis direction according to the sweep rate set by the user, it is typical that the one heartbeat period T1 of the M-mode image 70 does not match the one heartbeat period T2 of the contour model 90 merely by superimposing the contour model 90 on the M-mode image 70. However, because the contour model 90 is expanded or contracted in the time axis direction as described later, it is unnecessary to perform registration in the time axis direction strictly.

On the other hand, regarding a position in the depth direction, it is preferable to superimpose the contour model 90 with a certain degree of positional accuracy. For example, registration is performed by processing of matching the median of the M-mode image in the depth direction with the median of the contour model 90 in the depth direction, for example. Alternatively, the contour model 90 may be expanded or contracted in the depth direction so as to match the scale of the contour model 90 in the depth direction with the scale of the M-mode image in the depth direction.

The model expanding and contracting unit 30 expands the contour model 90 in the time axis direction so that the one heartbeat period T2 of the contour model 90 matches the one heartbeat period T1 of the M-mode image 70. As described above, because each node included in the contour model 90 has time information indicating a relative time point with respect to the one heartbeat period T2, in association with that expanding processing, each node is also moved in the time axis direction according to an expanded portion of the one heartbeat period T2. Because, in the present example, before processing by the model expanding and contracting unit 30 (that is, at the stage shown in FIG. 5(*a*)), the one heartbeat period T2 of the contour model 90 is shorter than the one heartbeat period T1 of the M-mode image 70, the contour model 90 is subjected to expanding processing. If the one heartbeat period T2 of the contour model 90 is longer than the one heartbeat period T1 of the M-mode image 70, the model expanding and contracting unit 30 contracts the contour model 90 in the time axis direction so that the one heartbeat period T2 of the contour model 90 matches the one heartbeat period T1 of the M-mode image 70.

As shown in FIG. 5(*b*), positions of the nodes included in the expanded contour model 102 become close to a plurality of target line segments included in the M-mode image 70. However, the contour model 102 is merely a model formed based on the past measurement data and the like, and therefore, at the stage shown in FIG. 5(*b*), the positions of the nodes included in the contour model 102 are not completely located on the plurality of target line segments included in the M-mode image 70.

Figure 6:
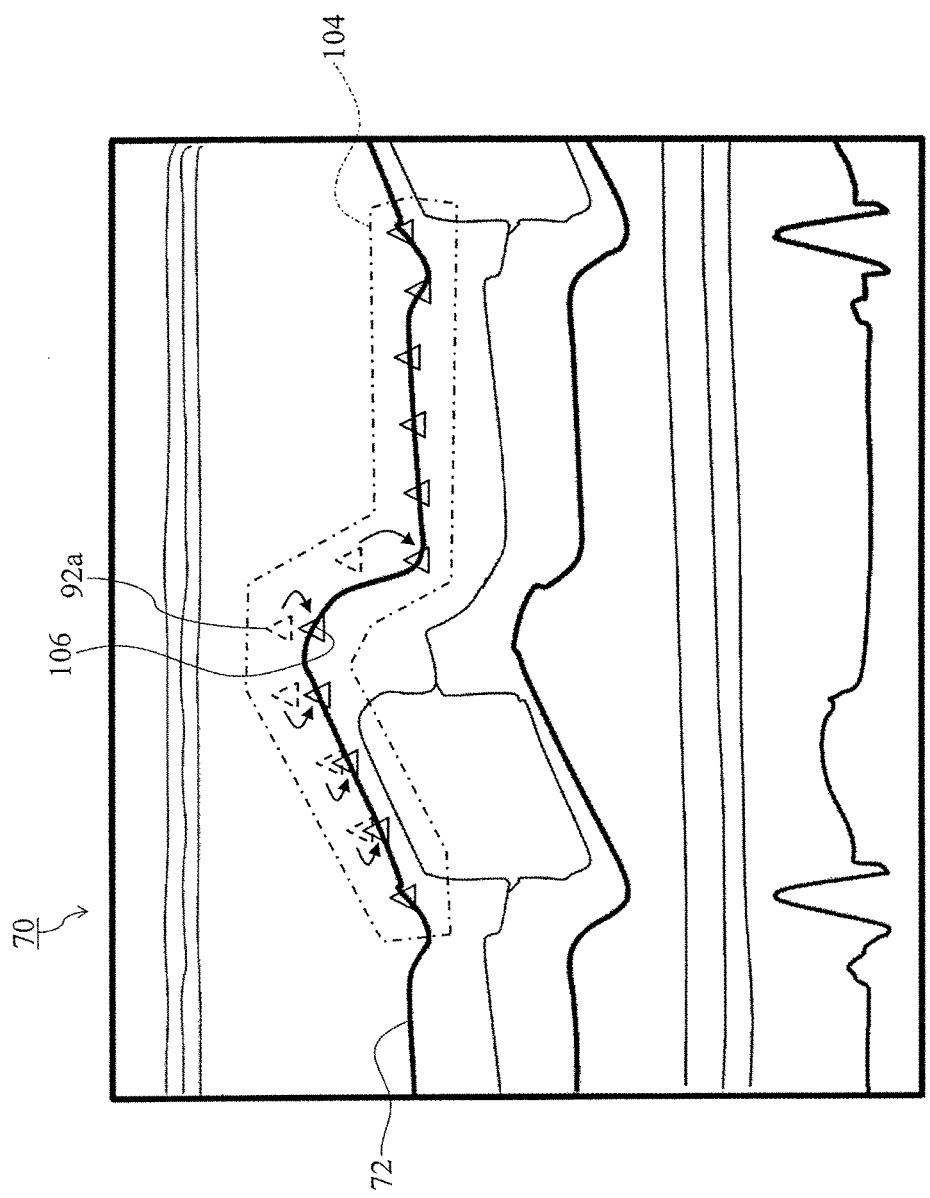
FIG. 6 is a conceptual diagram showing a state in which depth information of the contour model is changed.

FIG. 6 is a conceptual diagram showing a state in which depth information of the nodes of the expanded contour model 102 is changed. In FIG. 6, among the nodes included in the expanded contour model 102, the nodes other than those in the node string 104 corresponding to the contour line 72 of the anterior aortic wall 54 are omitted from the figure. The processing in the node position changing unit 32 serving as model deforming means will be explained based on an example where depth information of each node included in the node string 104 is changed.

The node position changing unit 32 performs image processing on the M-mode image 70, and performs edge search to detect a plurality of target line segments included in the M-mode image 70. Edge search is processing for extracting a position in the M-mode image at which the luminance sharply changes, and is conducted using a differential filter, for example. Because, as described above, a target line segment, which is a part of a contour line, is a high luminance line or a low luminance line, the contour line 72 can be extracted by edge search.

The node position changing unit 32 performs edge search for each node. More specifically, it performs edge search near each node using each node as a start point for edge search. For example, concerning a node 92*a* in FIG. 6, the node position changing unit 32 starts edge search from the position of the node 92*a*, performs edge search near the position, and ends edge search when it detects an edge 106. This enables the node 92*a* to be located on the edge 106. As a result of this processing, depth information of the node 92*a* is changed to information indicating the depth of the detected edge 106. By performing such processing on all the nodes, positions of the plurality of nodes included in the node string 104 become located on a target line segment, which is a part of the contour line 72 of the anterior aortic wall 54 in the M-mode image 70 obtained this time. By performing similar processing on the other node strings included in the contour model 102, a modified contour model including the plurality of nodes located on the target line segments included in the M-mode image 70 is formed.

As described above, in the present embodiment, the plurality of target line segments included in the M-mode image are extracted using the contour model 90. Because the plurality of nodes included in the contour model 90 are located near the plurality of target line segments included in the M-mode image, by using the plurality of nodes as edge search points, it is possible to reduce processing time to search positions of the target line segments.

In addition, an edge search range may also be set to be only within a predetermined range near each node. Because, as described above, the plurality of target line segments are considered to be near the nodes, it is highly likely that the contour line 72 is detected even if the search range is limited to near the nodes 92. Further, by restricting the search range, it becomes possible to detect the contour line faster when, for example, search is started in the direction opposite to the target line segment, when seen from the node. If no edge can be found in the predetermined range which is set first, the search area may be enlarged, to thereby perform processing such as edge search again.

Because edge search is performed only within the predetermined range near the nodes, edge search becomes less susceptible to noise included in the M-mode image 70. First, as long as there is no noise in the edge search range, there is no effect of noise on edge search. Second, although if edge search is performed near only one node, and, as a result, a wrong position is judged to be a contour position due to the effect of noise, edge search is performed separately for each of the other nodes, and therefore, there is no effect from false detection of that one node. In doing so, it is possible to further remove the effect of noise as a whole and extract the target line segments.

Further, since, in the present embodiment, the contour model 90 including the plurality of node strings is used, the plurality of target line segments can be extracted simultaneously. In this case, the contour model 90 has edge search start points (i.e., nodes) arranged in two dimensions in the time axis direction and the depth direction, and edge search is performed in parallel from each edge search start point. This enables the plurality of target line segments to be extracted more efficiently per heartbeat.

Figure 7:
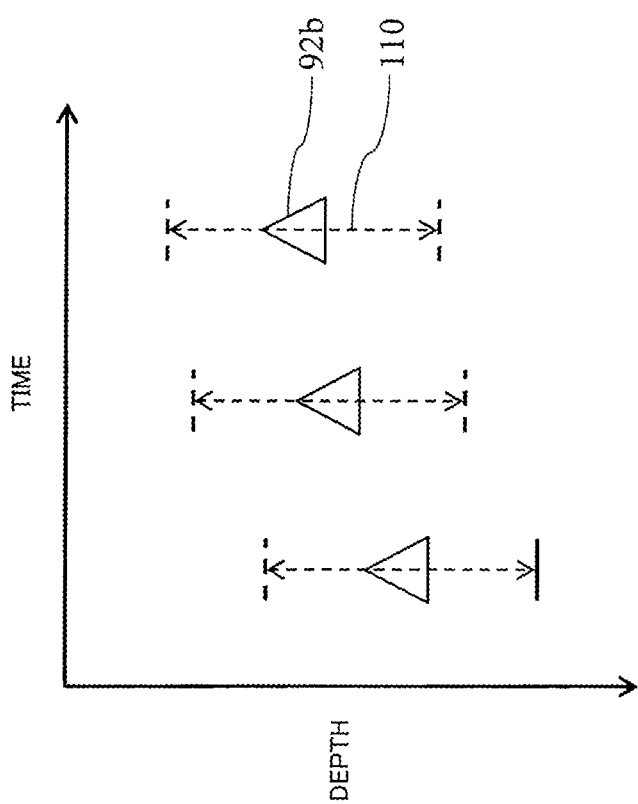
FIG. 7 is a diagram showing an example of ranges of edge searching positions.

FIG. 7 is a diagram showing an example of ranges of edge search positions. In the present embodiment, the node position changing unit 32 performs edge search in the direction parallel to the depth axis of the M-mode image (i.e., the direction vertical to the time axis). By performing edge search in the direction parallel to the depth axis, processing time required for edge search is shortened, and the intervals between the nodes in the contour model are maintained in the time axis direction. Namely, processing in the node position changing unit 32 does not change time information of each node of the contour model. As shown in FIG. 7, an edge search range 110 for a node 92b extends from the node 92b in the direction parallel to the depth axis. The width of the edge search range 110 may be determined as desired by the user. The edge search range 110 is preferably set to be a range having the node 92b as the center, but is not necessarily limited to this.

Figure 8:
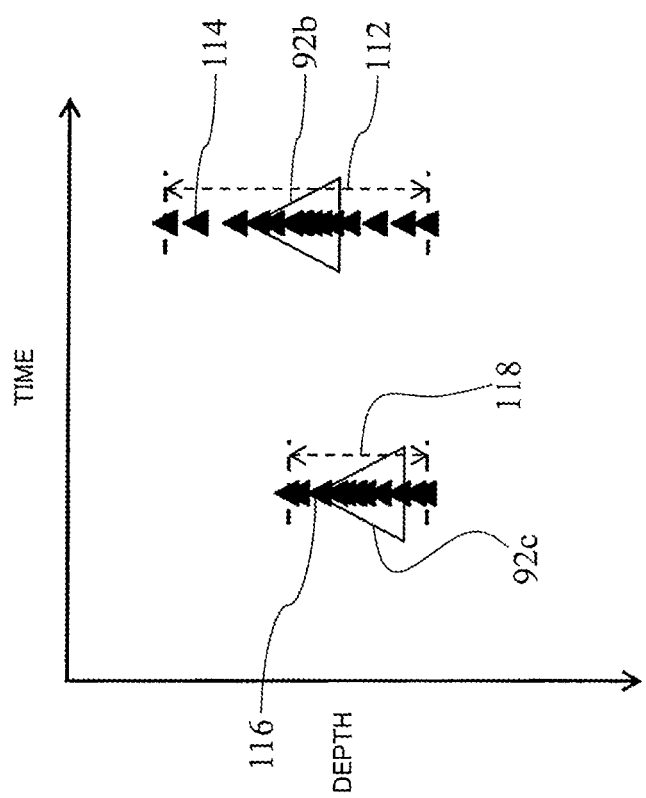
FIG. 8 is a diagram showing another example of ranges of edge searching positions.

FIG. 8 is a diagram showing another example of ranges of edge search positions. The edge search range may be determined based on depth information of nodes of a modified contour model formed in the past. In FIG. 8, the black triangles 114 indicate positions of the node 92b before the depth information is changed by the node position changing unit 32 and positions of the node 92b in modified contour models formed in the past. The positions indicated by the plurality of black triangles 114 are positions of the node 92b in the plurality of modified contour models; that is, history data of depth information of the node 92b. The past depth information of the node 92b indicates the depths at which contour lines of the anterior aortic wall are actually detected in M-mode images formed in the past, and therefore, if the edge search range is determined based on the distribution of history data pieces of the depth information of the node 92b, it would be highly likely that an edge is detected in that search range. In doing so, it becomes possible to set the edge search range appropriately; that is, in a range as narrow as possible, and reduce processing time further.

Further, as shown in FIG. 8, the nodes may differ in length of the edge search range. For example, if the distribution width of history data pieces of the depth information of the node 92b differs from the distribution width of history data pieces of depth information of a node 92c, their edge search ranges may be decided based on the respective distribution widths. As a result, an edge search range 112 corresponding to the node 92b and an edge search range 118 corresponding to the node 92c have different lengths.

Figure 9:
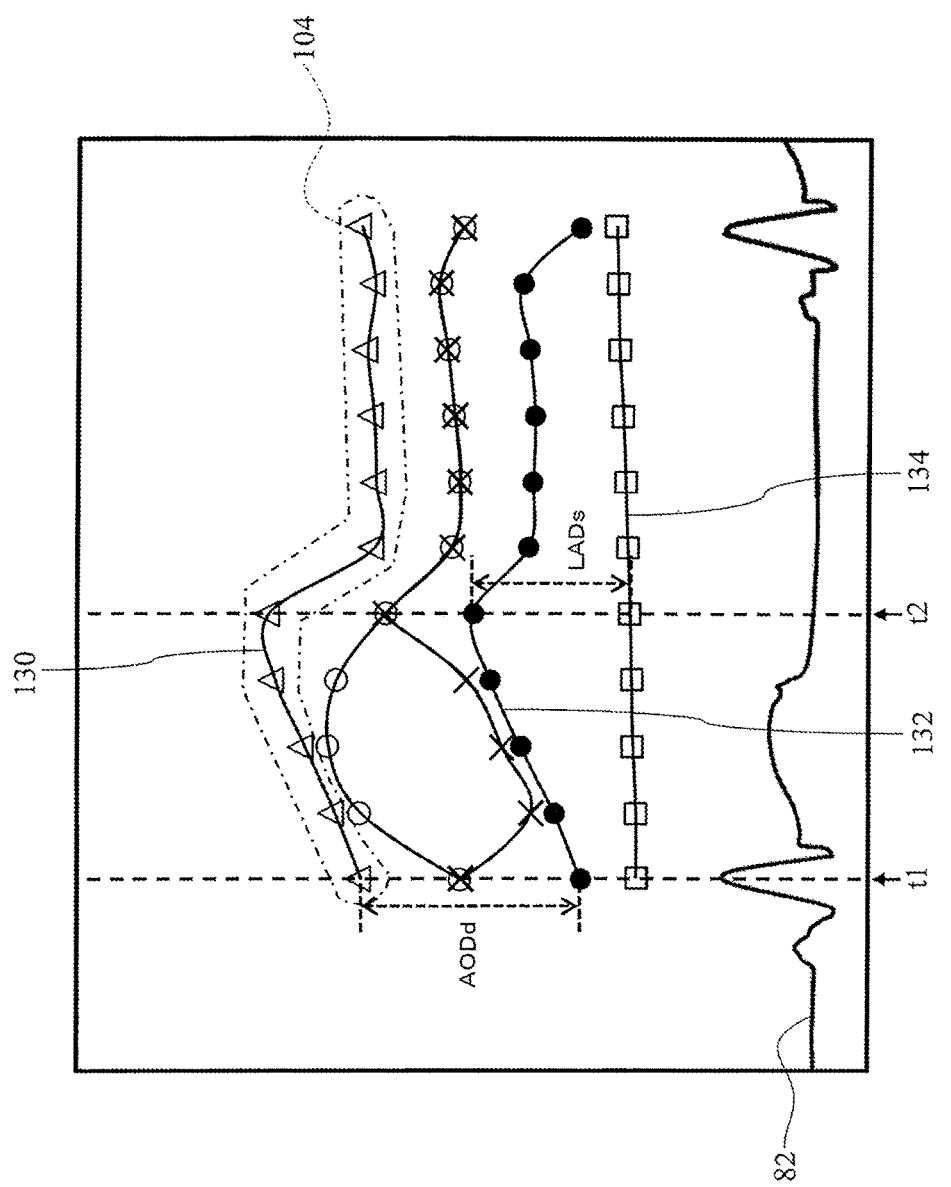
FIG. 9 is a diagram showing an example of interpolation processing between nodes included in each node string of a modified contour model.

FIG. 9 is a diagram showing an example of interpolation processing between nodes included in each node string of a modified contour model. When the node position changing unit 32 ends processing, and the modified contour model is formed, the tracing unit 34 performs tracing processing. Tracing processing is performed by interpolation processing between the nodes included in each node string of the modified contour model. For example, by interpolating between the nodes included in the node string 104 with curved lines, a trace line 130 that traces the target line segment which is a part of the contour line of the anterior aortic wall is formed. Similarly, by performing interpolation on the other node strings, trace lines that the trace target line segments are formed. Moreover, the nodes included in the modified contour model and the formed trace lines may also be displayed on the displaying unit, along with the M-mode image.

When the tracing unit 34 forms the trace lines, the measuring unit 36 measures the aortic diameter and the left atrial diameter based on the nodes included in the modified contour model or the formed trace lines. The measuring unit 36 specifies the end of cardiac diastole t1 and the end of cardiac systole t2 in the modified contour model, based on electrocardiographic data and the like. The measuring unit 36 then measures the interval between the trace line 130 of the anterior aortic wall and a trace line 132 of the posterior aortic wall at end-diastole t1, and sets this as the AODs (aortic diameter at end-diastole). In addition, the measuring unit 36 measures the interval between the trace line 132 of the posterior aortic wall and a trace line 134 of the posterior left atrial wall at end-systole t2, and sets this as the LADs (left atrial diameter at end-systole). Measured values of the AODs and the LADs and the LA/AO ratio between them are displayed on the displaying unit, along with the M-mode image. Although, in the present embodiment, the AODs and the LADs are measured, other items may also be measured based on the nodes included in the modified contour model or the formed trace lines.

FIG. 10 is a flowchart showing operational flow of the ultrasonic diagnostic device according to the present embodiment. FIG. 10 will be explained with reference to FIG. 1.

In step S10, the image forming unit 18 transmits and receives ultrasound to and from the subject, and forms an M-mode image based on a received signal from the probe 12.

In step S12, the extraction period specifying unit 28 specifies, in the formed M-mode image, an extraction period which is a period for extracting a target line segment, based on an electrocardiographic waveform formed from electrocardiographic data obtained by the electrocardiograph 20. In the present embodiment, one heartbeat period is specified as an extraction period.

In step S14, the model expanding and contracting unit 30 superimposes the contour model 24 on the M-mode image, and contracts the contour model 24 so that one heartbeat period of the contour model 24 matches the one heartbeat period of the formed M-mode image.

In step S16, the node position changing unit 32 performs edge search on the M-mode image, and extracts target line segments. In the present embodiment, edge search is performed for each node included in the contracted contour model 24, and edge search is performed from each node in the depth direction. The contour model 24 is deformed so that positions of the nodes included in the contour model 24 are located on edge positions extracted by edge search. In doing so, a modified contour model indicating the target line segments included in the M-mode image formed this time is formed.

In step S18, the tracing unit 34 performs interpolation processing on the node strings of the modified contour model, to thereby form trace lines that trace the target line segments included in the M-mode image.

In step S20, the measuring unit 36 performs desired measurement based on the nodes included in the modified contour model or the formed trace lines.

REFERENCE SIGNS LIST 10 ultrasonic diagnostic device, 12 probe, 14 transmitting and receiving unit, 16 cine memory, 18 image forming unit, 20 electrocardiograph, 22 storage unit, 24 contour model, 26 model applying unit, 28 extraction period specifying unit, 30 model expanding and contracting unit, 32 node position changing unit, 34 tracing unit, 36 measuring unit, 38 display control unit, 40 displaying unit, 42 control unit.

The invention claimed is:

1. An ultrasonic image processing device comprising:
a specifying unit that specifies, in an M-mode image including a contour line as a motion curve, an image portion that includes an extraction portion of the contour line; and
an extracting unit that applies a contour model including a node string to the image portion including the extraction portion, thereby extracting the extraction portion of the contour line, wherein
the extracting unit comprises
an initial setting unit that configures initial settings of the contour model for the image portion, and
a model deforming unit that performs contour search on the M-mode image for each of nodes included in the node string after the initial settings, thereby fitting the node string to the extracting portion and forming a modified contour model.

2. The ultrasonic image processing device according to claim 1, wherein
the initial setting unit comprises
a size adjusting unit that adjusts the size of the contour model in the time axis direction according to the length of the extraction portion in the time axis direction, and
a model positioning unit that positions on the image portion the contour model obtained after size adjustment.

3. The ultrasonic image processing device according to claim 2, wherein the model deforming unit performs the contour search in the distance direction for each node included in the positioned node string, the distance direction being vertical to the time axis direction.

4. The ultrasonic image processing device according to claim 3, wherein the model deforming unit performs, for each node included in the positioned node string, the contour search in a neighboring range of an initial set position of a node.

5. The ultrasonic image processing device according to claim 2, wherein
the initial setting unit further comprises a model generating unit that generates an original contour model based on a plurality of modified contour models formed in the past, and
the size adjusting unit adjusts the size of the original contour model in the time axis direction.

6. The ultrasonic image processing device according to claim 4, wherein the model deforming unit determines the size of the neighboring range in which the contour search is performed, based on a plurality of modified contour models formed in the past.

7. The ultrasonic image processing device according to claim 1, wherein
the M-mode image includes a plurality of contour lines,
the contour model includes a plurality of node strings for extracting a plurality of extraction portions of the plurality of contour lines, and
the model deforming unit performs contour search for each node included in the plurality of node strings, and causes the plurality of node strings to fit the plurality of extraction portions, respectively.

8. The ultrasonic image processing device according to claim 1, further comprising a tracing unit that generates a trace line which simulates the extraction portion, by interpolation processing based on the node string fitted to the extraction portion.

9. The ultrasonic image processing device according to claim 1, wherein the specifying unit specifies the image portion based on heartbeat information of a subject.

* * * * *